United States Patent [19]

Kataoka et al.

[11] Patent Number: 4,617,837
[45] Date of Patent: Oct. 21, 1986

[54] SPEED CHANGE DEVICE FOR MEDICAL HANDPIECE

[75] Inventors: Kenzo Kataoka, Otsu; Hiroo Watanabe, Kyoto, both of Japan

[73] Assignee: Kabushiki Kaisha Morita Seisakusho, Kyoto, Japan

[21] Appl. No.: 701,086

[22] Filed: Feb. 13, 1985

[30] Foreign Application Priority Data

Feb. 18, 1984 [JP]  Japan .................................. 59-29244

[51] Int. Cl.[4] ............................................ F16H 57/10
[52] U.S. Cl. ........................................ 74/785; 74/198; 74/750 R
[58] Field of Search ..................... 74/198, 750 R, 785, 74/798

[56] References Cited

U.S. PATENT DOCUMENTS

| 2,536,803 | 1/1951 | Gleason | 74/798 X |
| 3,631,742 | 1/1972 | Hoffmeister | 74/798 |
| 3,641,842 | 2/1972 | Hewko | 74/798 X |
| 3,793,907 | 2/1974 | Nakamura et al. | 74/798 |
| 4,074,591 | 2/1978 | Dick | 74/785 X |
| 4,286,480 | 9/1981 | Dickie | 74/785 |

FOREIGN PATENT DOCUMENTS

| 529737 | 8/1956 | Canada | 74/750 R |
| 45-40802 | 12/1970 | Japan | 74/798 |
| 58-46252 | 3/1983 | Japan | 74/798 |
| 2103735 | 2/1983 | United Kingdom | 74/750 R |

Primary Examiner—Kenneth J. Dorner
Assistant Examiner—Dwight G. Diehl
Attorney, Agent, or Firm—Koda and Androlia

[57] ABSTRACT

A speed change device arranged such that a driving shaft connecting with a driver and a tool working shaft connected with a driven tool are connected with each other for transmission of torque in the no speed change mode or in the speed change (acceleration or deceleration mode and wherein a manipulating sleeve on the outer periphery of the handpiece case is used for selecting either the no speed change or the speed change mode thereby saving the expense of providing alternative devices for the individual modes of torque transmission.

2 Claims, 13 Drawing Figures

SPEED CHANGE DEVICE FOR MEDICAL HANDPIECE

BACKGROUND OF THE INVENTION

1. Field of the Invention

The present invention relates to a speed change device for a transmission under no speed change or under acceleration or deceleration of the torque of a driving shaft connecting an electric or pneumatic driving unit to a driven shaft (hereinafter referred to as "working shaft").

2. Prior Art

For enabling mechanical transmission of torque from a driving shaft to a working shaft it was hitherto necessary to provide several speed change devices of either a gear type each thereof having a fixed speed change ratio or a bail planetary type so that the one best suited for the particular work can be chosen. For the user, it was not only troublesome but also meant an increased financial burden. Another problem was that it occupied a large portion of the limited clinical space.

SUMMARY OF THE INVENTION

The present invention was made in view of the situation described above and provides a highly effective and easy to use speed change device for a medical handpiece for transmission in any one of the modes of no speed change, acceleration or deceleration.

BRIEF DESCRIPTION OF THE DRAWINGS

In the annexed drawings given for illustration of a preferred embodiment of the present invention.

DETAILED DESCRIPTION OF THE INVENTION

Figure 1:
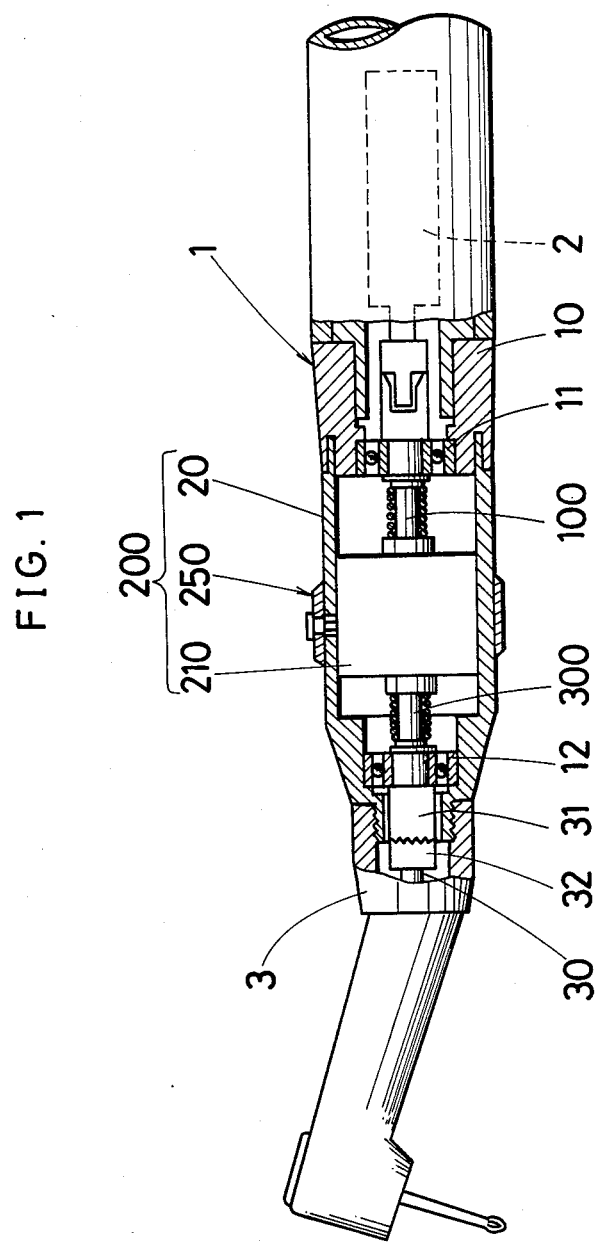
FIG. 1 is a partially broken vertical sectional view of a handpiece.
Figure 2:
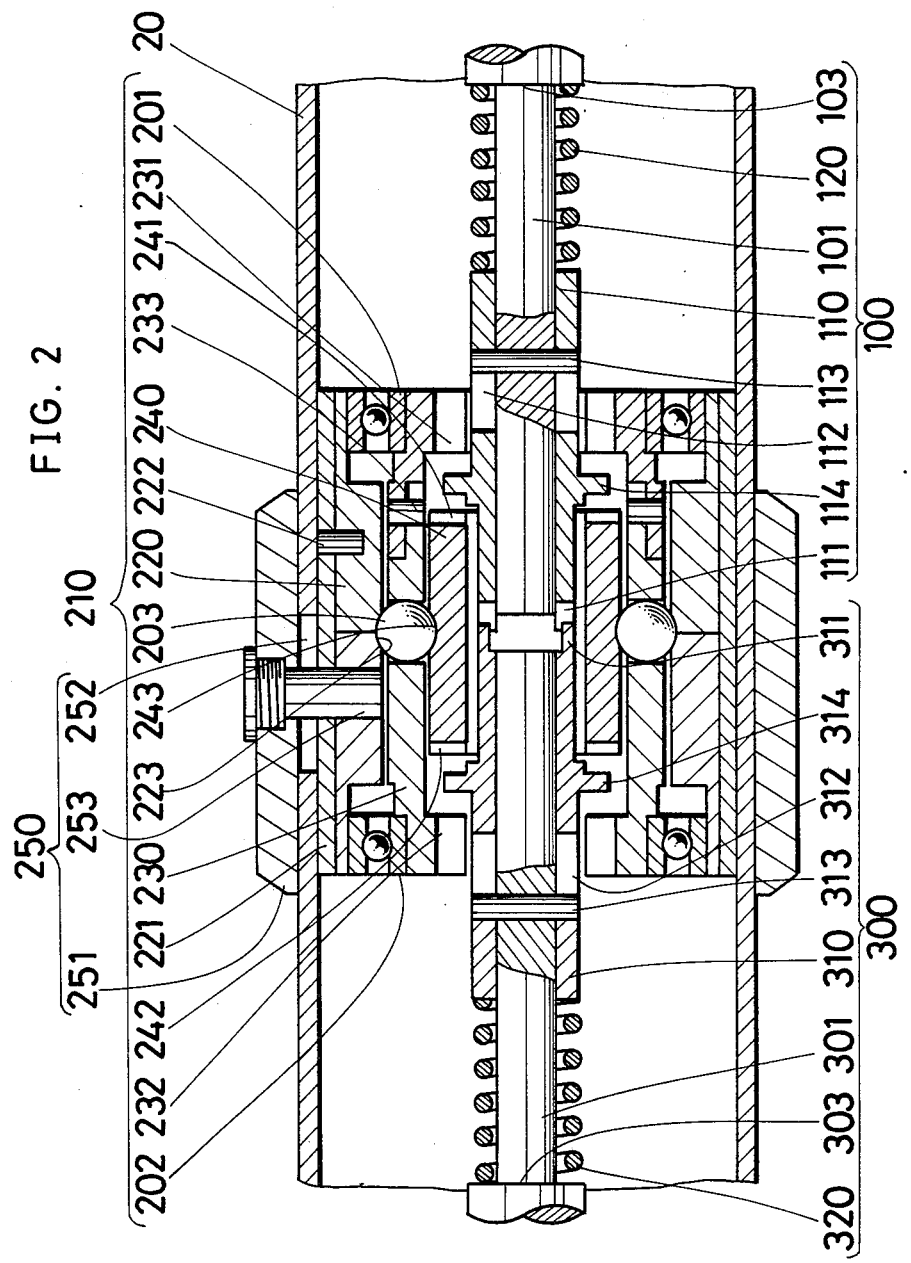
FIG. 2 is a vertical sectional view of speed change device of the present invention in the no speed change mode.

As seen from a dental handpiece of the contra-angle type, the speed change device 200 of the present invention is so designed that two rotary shafts 100 and 300, i.e. a driving shaft 100 and working shaft 300 carried by ball bearings 11 and 12 respectively so as to be freely rotatable concentrically are manipulatably connected with each other with the rotational speed of the rotary shaft 300 the same as, faster than or slower than the shaft 100 and these three speed connections shall be referred to as "no speed change", or accelerated or decelerated modes.

Figure 8:
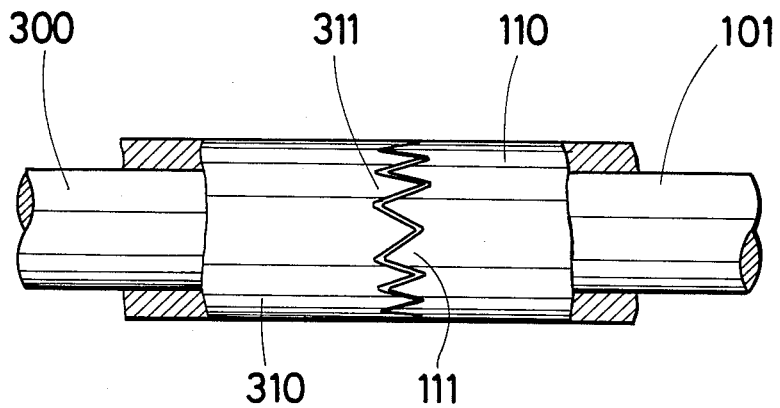
FIG. 8 is a partially cutaway view showing the engaging portion of the above-mentioned sleeve.

A planetary torque transmission mechanism 210, which enables transmission of the torque of the driving shaft 100 to the working shaft 300 under no speed change, acceleration or deceleration, is mounted on and between the driving shaft 100 and working shaft 300 in a case 20. On the outer periphery of this case 20 is provided a manipulating or switching means 250 for selecting either the no speed change, the acceleration or the deceleration mode. Through the manipulating means 250, the aforesaid driving shaft 100 and working shaft 300 are connected directly or at least either the planetary torque transmission mechanism 210 or the aforesaid driving shaft 100 or working shaft 300 is shifted to disconnect the shafts 100 and 300 and these two shafts are then connected indirectly through the planetary torque transmission mechanism 210. The driving shaft 100 is rotary driven at a fixed speed by a driving means 2 such as a micro-motor. The shaft 100 is supported through a ball bearing 11 to a case 10 of a body housing 1 and over the shaft 100 is mounted a cylindrical engaging sleeve 110 via pin 113 so as to rotate together with the shaft 100 and be slidable in the axial direction through a slot 112 and the pin 113 fitted therein. The end 111 of the sleeve 110 is formed into a zigzag like a fork, as shown in FIG. 8, which end 111 can be meshed with its counterpart 311 on the working shaft side (to be described later).

Figure 9:
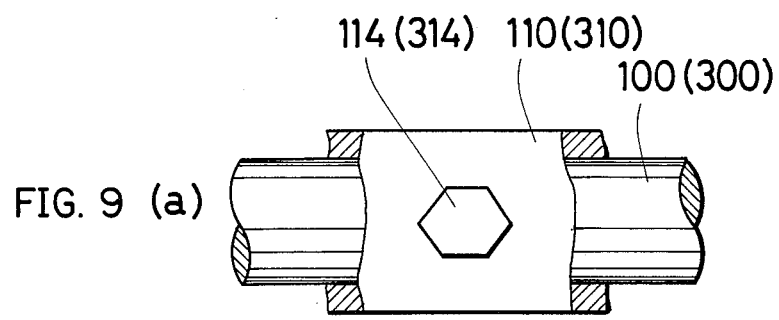
FIGS. 9(a) and (b) are a plan view and a side view showing the engagaing projection of the above-mentioned sleeve.
Figure 9:
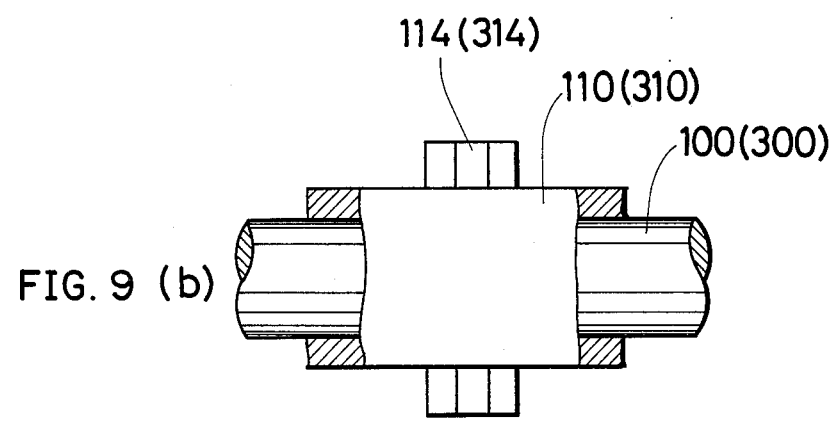

The spring 120 is formed as a coil and is set between the shoulder 103 of the driving shaft 100 and the rear end of the engaging sleeve 110 so as to urge the engaging sleeve 110 toward its engaging end. On the outer periphery of the engaging sleeve 110, regular hexagonal projections 114 as shown in FIGS. 9(a) and (b) are disposed with at least its two opposing sides parallel to the sleeve's axis, and these serve for selective engagement with the planetary torque transmission mechanism 210 as described later on. The working shaft 300 is driven directly by the driving shaft 100 in the no speed change mode or driven through the planetary torque transmission mechanism 210 in the speed change mode. The shaft 300 is supported in the case 20 by ball bearings 12 engaged through couplings 31 and 32 with a tool working shaft 30 of a head of the contro-angle type 3 screwed onto the case 20. At the rear end of a small diameter part 301 of the working shaft 300, an engaging cylindrical sleeve 310 of the same construction as the engaging sleeve 110 is mounted over the shaft 300 and the sleeve 310 is urged to be engaged by a spring 320 provided between the shoulder 303 and the forward end of the sleeve 310. The rear end portion 311, too, is formed into a zigzag and this rear end portion 311 is to be directly engaged with the engaging sleeve 110 in the no speed change mode. The engaging cylindrical sleeve 310 is fitted over the shaft 300 via pin 313 so as to rotate together with the shaft 300 and be slidable in the axial direction through a slot 312 and the pin 313 fitted therein. As seen from FIGS. 9(a) and (b), regular hexagonal projections 314 with at least their two sides preferably parallel with the axial direction of the shafts 100 and 300 are provided for selective engagement with the planetary torque transmission mechanism 210.

Figure 7:
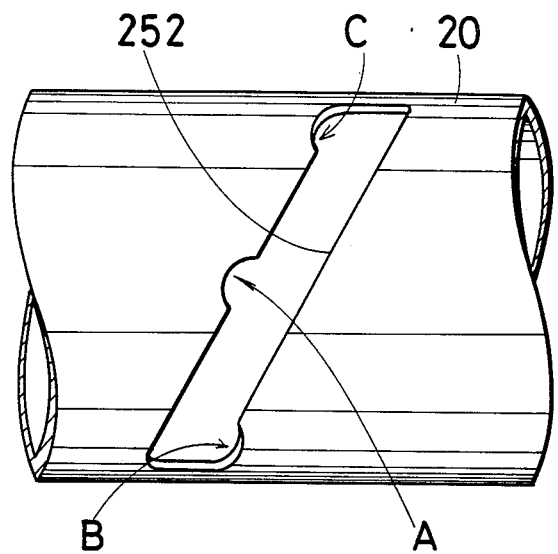
FIG. 7 is a side view given to show a switching sleeve of the speed change device.

The planetary torque transmission mechanism 210 is of the ball planetary type, in which inside the case 20 the outer race 220 is carried to be freely movable longitudinally, a ball retainer 230 with i.e. eight equidistant holes for retaining the balls 203 in rolling contact with the peripheral groove 223 provided on the inside of the race 220 and the inner race 240 in rolling contact with the balls 203 at the peripheral groove 243 surrounded concentrically by the ball retainer 230. On the external periphery of the case 20 of the speed change device is provided a manipulating means 250 for selecting the planetary torque transmission mechanism 210 in either the no speed change mode or the speed change mode. The manipulating means 250 consists of a short rotatable sleeve 251 set on the case 20, which has provided therein a cam slot 252 diagonal with pockets for acceleration (arrow B), no speed change (arrow A) and deceleration (arrow C) as shown in FIG. 7 and an actuating pin 253 screwed into the sleeve 251 and set in the outer race 220 past the slot 252. Hence, when the rotatable sleeve 251 is turned with respect to the cast 20, the actuating pin 253 is moved longitudinally while being guided by the cam slot 252, and with the rotatable sleeve 251 and the outer race 220, ball retainer 230, balls 203 and bearings 201 and 202 are all together moved longitudinally so as to select any one of the no speed change or the speed change modes. As manipulating means 250 one capable of direct longitudinal movement instead of rotational movement may be also selected, and thus the embodiment shown is not so restricted.

The outer race 220 is split in two so as to be fabricated by connecting sleeve 221 and facilitate assembly of the planetary torque transmission mechanism 210. Two pins 253 and 222 are provided as anti-slippage means for the race 220. A ball retainer 230 is held inside the outer race 220 at both ends by bearings 201 and 202 so as to be freely rotatable and slidable in the longitudinal direction by the ball 203. Inside peripheral faces at both ends there are provided grooves 231 and 232 equidistant about the periphery so as to selectively engage with projections 114 and 314 of the sleeves 110 and 210 from outside, as shown in FIGS. 2 through 5. The retainer 230, too, consists of separate components, which are assembled by means of a pin 233. The inner race 240 is peripherally rotatable as well as axially slidable together with the ball retainer 230 and is assembled between the opposing projections 114 and 314 of the engaging sleeves 110 and 310 so as to surround the clamping portion of the engaging sleeves 110 and 310. There are provided notches 241 and 242 which engage from inside with either of the projections 114 and 314 as shown in FIGS. 2 through 4 and FIG. 6 at both ends equidistant about the periphery.

Figure 3:
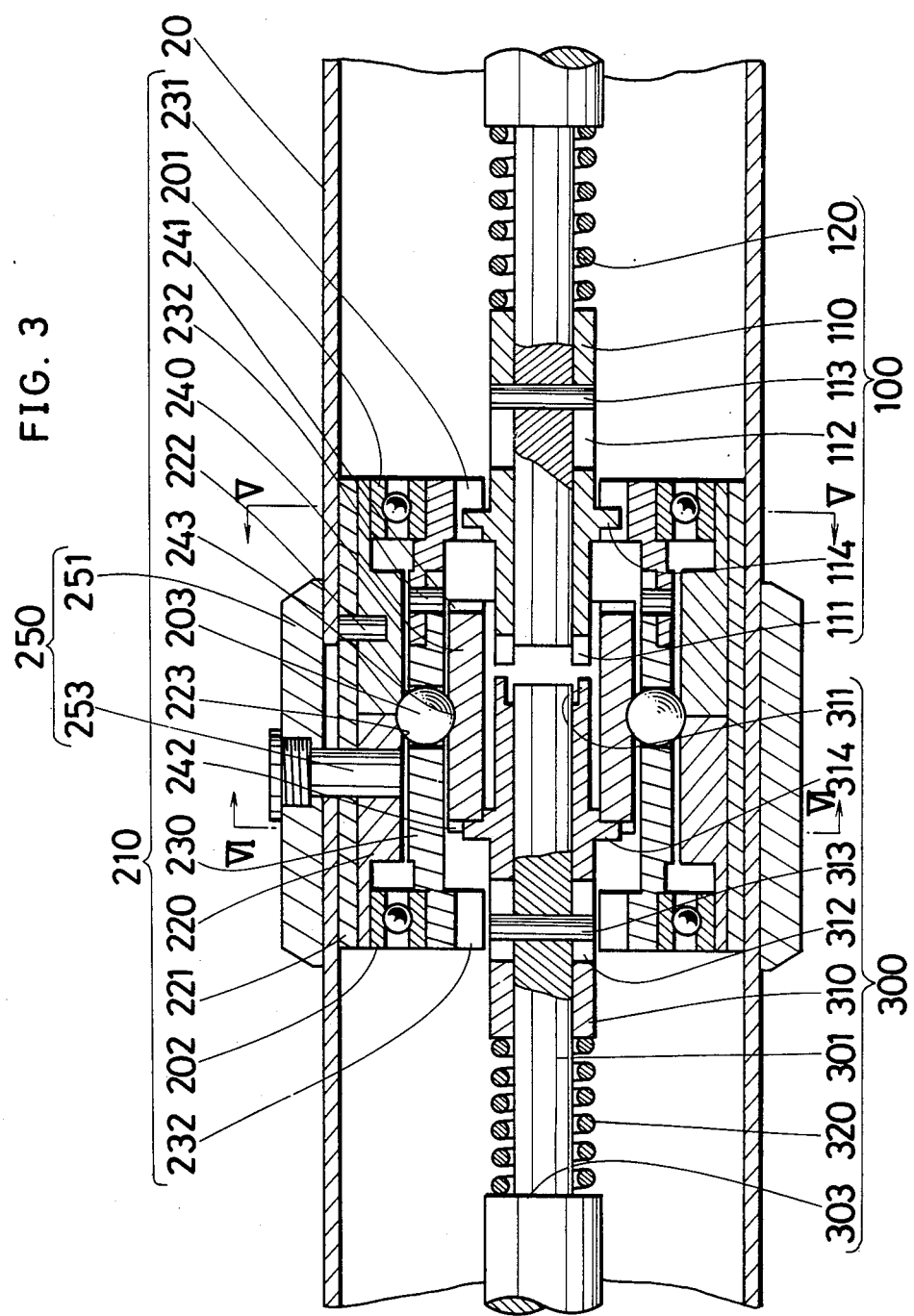
FIG. 3 is a vertical sectional view of the same in the acceleration mode.
Figure 4:
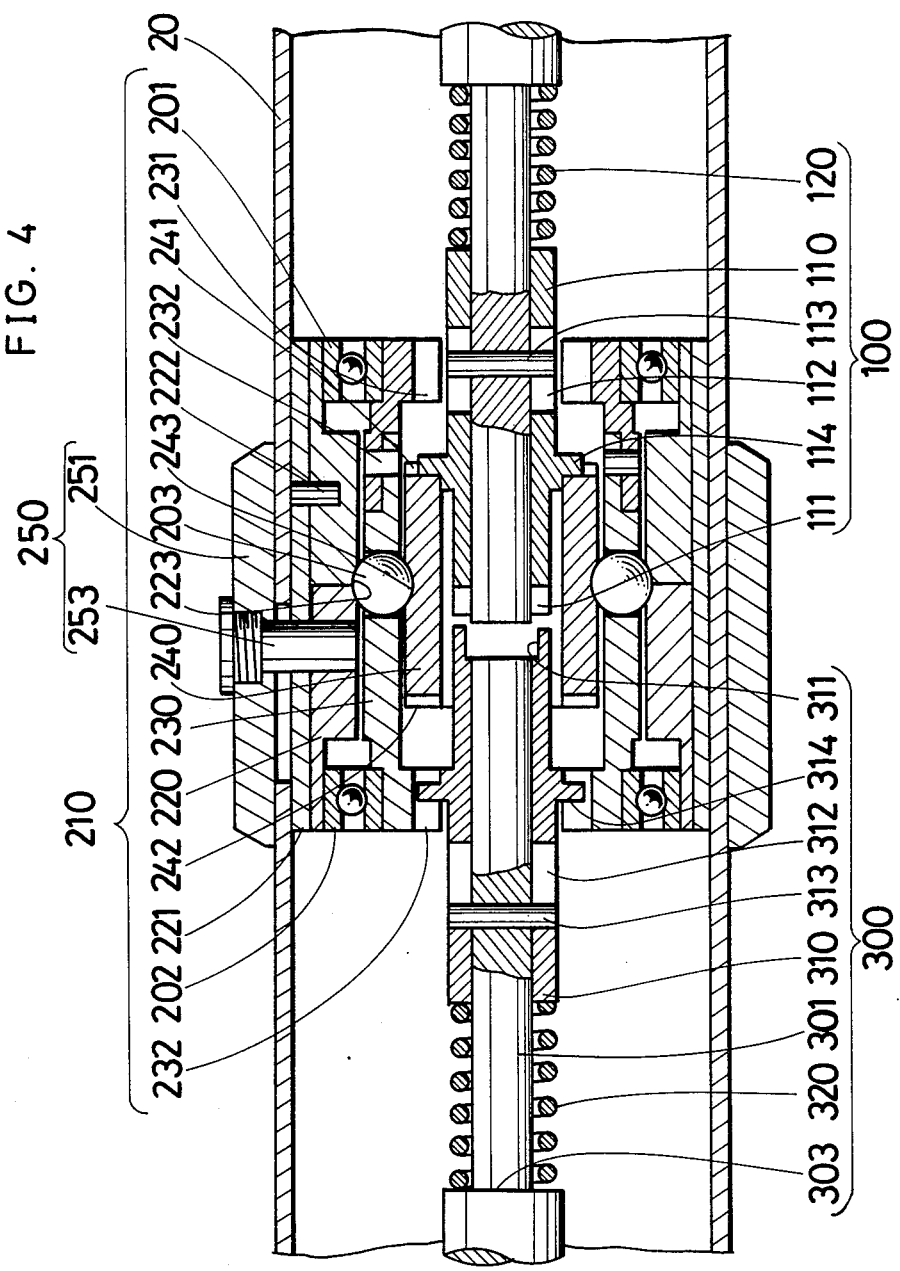
FIG. 4 is a vertical sectional view of the same in the deceleration mode.
Figure 5:
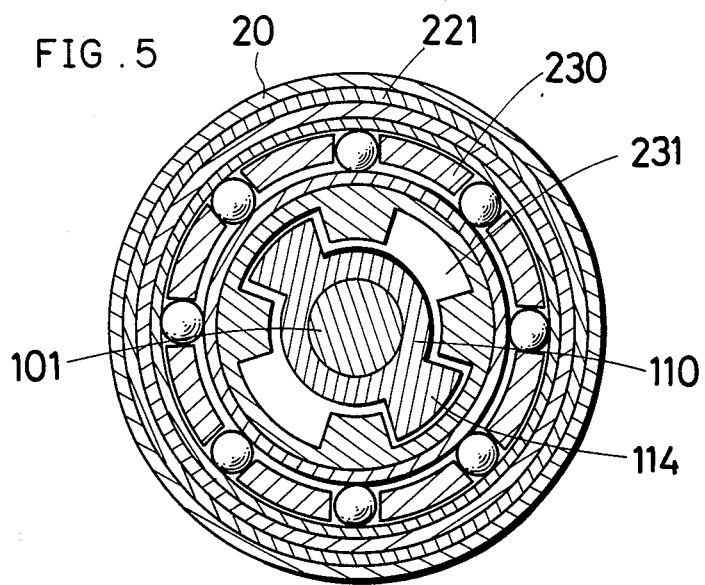
FIG. 5 is a cross-sectional view taken along the line V—V of FIG. 3.
Figure 6:
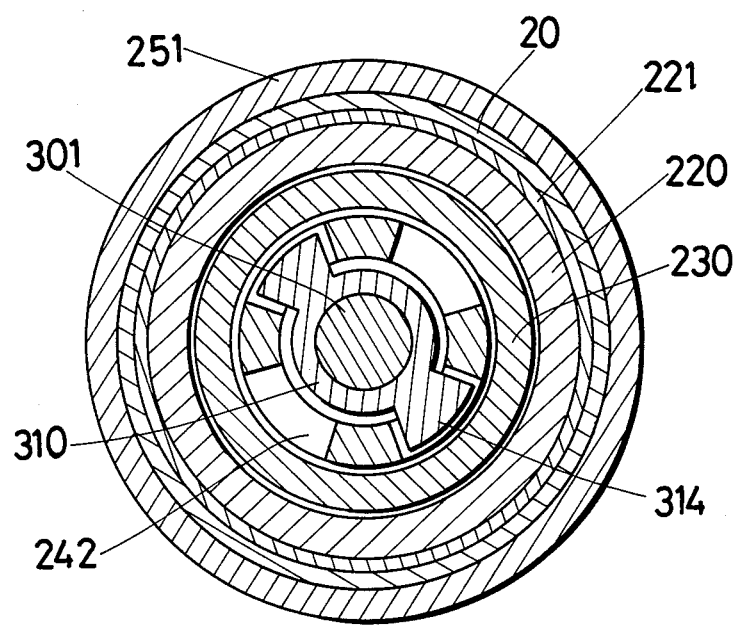
FIG. 6 is a cross-sectional view taken along the line VI—VI of FIG. 3.
Figure 10:
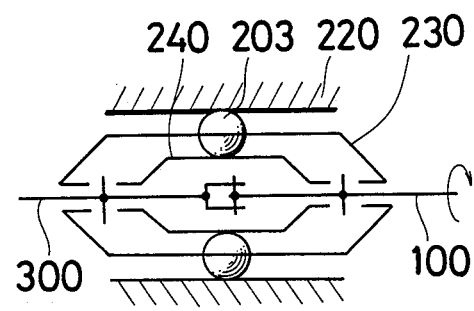
FIGS. 10(a), (b) and (c) are illustrative views showing the speed change device in the no speed change mode, acceleration mode and deceleration mode respectively.
Figure 10:
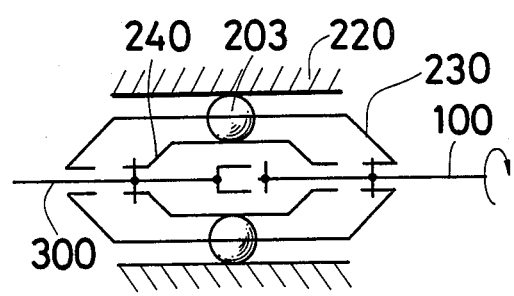
Figure 10:
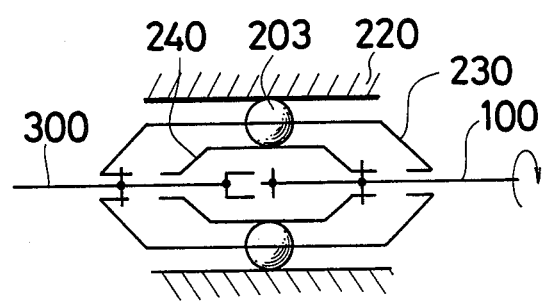

Explained below is the ways in which the speed change device of the above composition is used. Principally the engaging situation for each mode is as shown in FIGS. 10(a), (b) and (c), and particularly a concrete illustration for the no speed change mode in FIG. 10(a) is given in FIG. 2. As shown in the figure, the engaging sleeves 110 and 310 for the driving shaft 100 and the working shaft 300 are directly coupled as shown in FIG. 8 but are free from the retainer 230 and inner race 240. Hence the rotational speed of the driving shaft 100 is transmitted unchanged to the working shaft 300. If the speed has to be varied in this mode, however, it is feasible by changing the input voltage of the micromotor as driver 2 or by changing the input pneumatic pressure of the air motor. A concrete illustration of the acceleration mode shown in FIG. 10(b) is as shown in FIG. 3. When the handpiece is held with its driving part nearer to the operator as it is normally, and the rotatable sleeve 251 is driven clockwise, the actuating pin 253 is shifted by the diagonal slot 252 toward the working shaft 300. Thus the transmission mechanism as a whole is shifted against the spring 320 on the working shaft side. As as a result, first the projection 314 engages in the notch 242 on the working shaft side with simultaneous engagement of the projection 114 in the groove 231 on the driving shaft side. As it is shifted further, the engaging sleeve 310 is pushed to thereby simultaneously disengage from the engaging sleeve 110. In this situation the rotational speed of the driving shaft 110 is transmitted via retainer 230, ball 203 and inner race 240 to the working shaft 300. With the diameter of the contact face of the inner peripheral groove 243 of the inner race as A and the diameter of the contact face of the peripheral groove 223 of the outer face as B, the then acceleration rate is $(A+B)/A$. The extent of the acceleration mode can be made still wider with the possibility of changing the rotational speed of the driver 2. A concrete illustration of the deceleration mode of FIG. 10(c) is as shown in FIG. 4. When the handpiece is held in the normal state with its driver side toward the operator and the rotatable sleeve 251 and the no speed change position is turned counter-clockwise, the actuation pin 253 is guided by the diagonal slot 252 toward the driving shaft 100 side. As a result, the transmission mechanism 210 as a whole is shifted against the spring 120. Therefore, first the projection 114 is engaged with the notch 241 on the driving shaft side with simultaneous engagement of the projection 314 with the groove 232 on the working shaft side. As it is shifted further, the engaging sleeve 110 is pushed to thereby make simultaneous disengagement from the engaging sleeve 310 on the working shaft side. In this situation the rotational speed of the driving shaft 100 is transmitted via the inner race 240, the ball 203 and the retainer 230 to the working shaft 300, the then deceleration rate being $A/(A+B)$. The extent of the deceleration mode can be still wider when the possibility of changing the rotational speed of the driver 2 is taken into consideration.

Each ball 203 is closely circumscribed and inscribed with respect to the concave inner face of the peripheral grooves 223 and 243 of the inner race 240 and the outer race 220 by the resilience of the spring 120 and 320. Further the ball is retained by the retainer 230; hence, in the speed change (acceleration or deceleration) mode the torque of the driving shaft 100 is transmitted via retainer 230 with balls 203 rolling on the concave inner face of the peripheral groove 223 of the outer race 220 which are caused to be also in rolling contact with that of the peripheral groove 243 of the inner race. Since this mode of transmission of the shaft torque by the ball planetary mechanism is by the use of rolling balls 203 there is practically no friction induced heating and the torque transmission proceeds very smoothly unlike its gear counterpart which is subject to damage of the gear teeth, vibration, etc.

In the present embodiment the handpiece is of the contra-angle type, but needless to say, this invention is applicable to a handpiece of the straight type.

As mentioned above, it is possible by the use of the speed change device 200 to transmit the torque of the driving shaft 100 in the no speed change mode, acceleration mode or deceleration mode by means of the rotatable sleeve 251 set on the case 20 and by the use of a single speed change device. Thus, according to the present invention, the effort of changing the speed change device so as to suit the particular conditions every time the speed change ratio varies can be saved as well as the expense of providing a multiplicity of speed change devices and also the clinical space. The present invention, therefore, contributes a great deal to the progress of dental techniques.

The use of ball planetary mechanism as represented by speed change device 200 enables the provision of a speed change device free of vibration or noise and is also highly durable.

It should also be understood that the foregoing relates to only the scope of the invention defined by the applied claims rather than by the description preceding them, and all changes that fall within the meets and bounds of the claims, or equivalence of such meets and bounds are therefore intended to be embraced by the claims.

We claim:

1. A speed change device for a medical handpiece arranged such that first and second rotary shafts are connectably carried by bearings and freely rotatably in a case of a handpiece and are connected for transmission of torque at the same, faster or slower speed as the first rotary shaft, said speed change device being characterized in that:

it comprises on and between said first and second rotary shafts in said case a planetary torque transmission mechanism, which enables transmission of torque of said first rotary shaft on the driving side to said second rotary shaft on the driven side at the same, faster or slower speed as the first rotary shaft, said planetary torque transmission mechanism is of the ball planetary type and comprises an outer race freely slidable axially, a ball retainer retaining a ball free to roll and in rolling contact with a peripheral groove inside said race and inner race whose outer peripheral groove corresponds to said peripheral groove of said outer race;

on the outer periphery of said case a manipulating means for selecting either the same, faster or slower speed as the first rotary shaft whereby through manipulation of said manipulating means said first and second rotary shafts are connected directly, connected by said planetary torque transmission mechanism or shifted for disconnecting said first and second rotary shafts so that said first and second rotary shafts are then connected indirectly through said planetary torque transmission mechanism; and said first and second rotary shafts are provided with first and second engaging sleeves fitted respectively thereover, said first and second engaging sleeves being mutually engageable at face-to-face ends, peripherally rotatable together with said first and second rotary shafts and slidable in an axial direction via slots, pin means respectively fitted in said slots, and first and second springs for urging said first and second sleeves into engagement.

2. A speed change device for a medical handpiece according to claim 1, wherein said planetary torque transmission mechanism engages said first rotary shaft with said ball retainer by means of said first engaging sleeve and also engages said inner race with said second rotary shaft by means of said second engaging sleeve in a mode wherein the second rotary shaft rotates faster than said first rotary shaft, and engages the first rotary shaft with said inner race by means of said first engaging sleeve while simultaneously engaging said ball retainer with said second rotary shaft by means of said second engaging sleeve when in a mode wherein the second shaft rotates slower than said first rotary shaft.

* * * * *